United States Patent [19]

Satomi et al.

[11] 3,997,526
[45] Dec. 14, 1976

[54] AMIDO PHOSPHOROTHIOLATE PESTICIDE

[75] Inventors: Takeo Satomi, Nishinomiya; Naganori Hino; Masachika Hirano, both of Toyonaka; Kunio Mukai, Nishinomiya; Hideo Sakamoto, Toyonaka; Ryo Yoshida, Minoo, all of Japan

[73] Assignee: Sumitomo Chemical Company, Limited, Osaka, Japan

[22] Filed: Nov. 15, 1973

[21] Appl. No.: 416,205

[30] Foreign Application Priority Data

Nov. 30, 1972 Japan .......................... 47-120438
Nov. 30, 1972 Japan .......................... 47-120439
Apr. 26, 1973 Japan .......................... 48-48234

[52] U.S. Cl. ................................. 260/239 B; 71/87; 424/200; 260/283 S; 260/289 R
[51] Int. Cl.$^2$ ....................... C07F 9/60; C07F 9/65
[58] Field of Search ................................ 260/239 B

[56] References Cited

UNITED STATES PATENTS

| 3,134,801 | 5/1964 | Sehring et al. ............... 260/293.85 |
| 3,806,560 | 4/1974 | Kishino et al. ............... 260/293.85 |

FOREIGN PATENTS OR APPLICATIONS

| 710,340 | 5/1965 | Canada ......................... 260/239 B |
| 1,812,497 | 8/1969 | Germany ...................... 260/239 B |

OTHER PUBLICATIONS

Itskova et al., Zh. Obshch. Chim., vol. 38, pp. 2471–2475, (English Edition), (1968).

*Primary Examiner*—Alton D. Rollins
*Attorney, Agent, or Firm*—Wenderoth, Lind & Ponack

[57] ABSTRACT

Amidophosphorothiolate compounds, for example N-(O-methyl-S-n-propyldithiolphosphorylacetyl)-tetrahydroquinoline, are provided which have herbicidal activity.

3 Claims, No Drawings

AMIDO PHOSPHOROTHIOLATE PESTICIDE

The present invention relates to new compounds, herbicidal, insecticidal, acaricidal and nematocidal compositions characterized by containing a new phosphorothiolate derivative as an active ingredient and the preparation thereof.

More particularly, the present invention provides 1. a new phosphorothiolate derivative of the formula

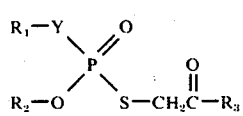
(I)

wherein $R_1$ is lower alkyl, lower alkenyl, lower alkynyl or a group

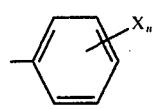

(in which X is lower alkyl, halogen or hydrogen, $n$ is an integer of 0 to 5); $R_2$ is lower alkyl, lower alkenyl or lower alkynyl; $R_3$ is a radical of the formula,

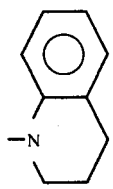

or a radical of the formula,

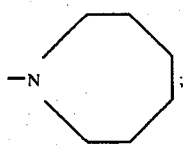

and Y is oxygen or sulfur, 2. the preparation of the compound of the formula (I) characterized in condensing a salt of thiophosphate of the formula;

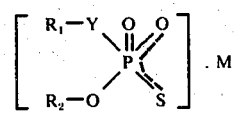
(II)

wherein $R_1$, $R_2$ and Y are the same as defined above, and M is an alkali metal atom, with a halogenated acetoamide compound of the formula;

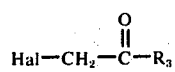
(III)

wherein $R_3$ is the same as defined above, and Hal is a halogen atom, and 3. a herbicidal, insecticidal, acaricidal and nematocidal composition containing the compound of the formula (I) as an active ingredient.

A preferred range of the compound of the formula (I) is as follows;

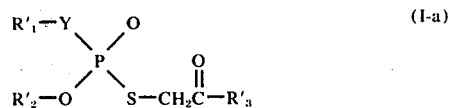
(I-a)

wherein $R'_1$ is straight or branched chain $C_1 - C_6$ alkyl, allyl, phenyl, $C_1 - C_2$ alkyl-substituted phenyl or chloro-substituted phenyl; $R'_2$ is $C_1 - C_4$ alkyl; Y is oxygen or sulfur; and $R'_3$ is a radical of the formula,

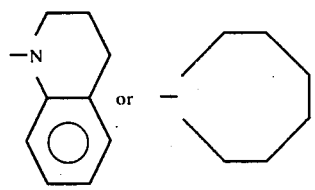

And a preferred compound as a herbicide is as follows;

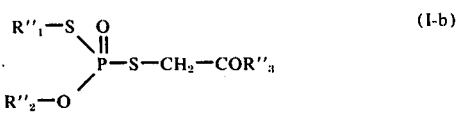
(I-b)

wherein $R''_1$ is a lower alkyl, lower alkenyl or lower alkynyl; $R''_2$ is an alkyl group; $R''_3$ is a radical of the formula,

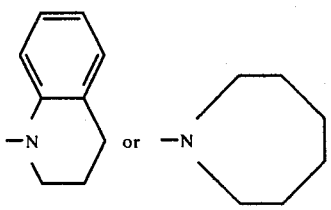

Especially a compound of the formula,

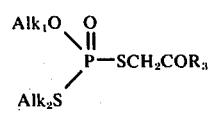
(I-c)

wherein $Alk_1$ is a $C_1 - C_4$ alkyl; $Alk_2$ is a $C_1 - c_5$ alkyl; $R_3$ is a radical of the formula,

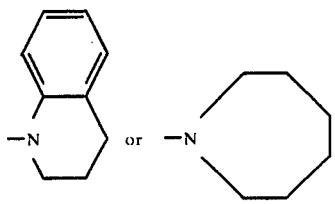

has the most excellent herbicidal activity of the compounds represented by the formula (I – b) without phytotoxity and toxicity to warm-blooded animals.

The new active ingredient of the present invention displays a strong herbicidal activity not only when used in both a pre-emergence treatment ad a foliage treatment of weeds, but also on various kinds of weed including grassy weeds such as barnyard grass (*Echinochloa Crus-galli*), large crabgrass (*Digitaria sanguinalis*), goose grass (*Eleusine indica*), water foxtail (*Alopecurus aequalis*) and annual bluegrass (*Poa annua*); broad-leaved weeds such as redroot pigweed (*Amaranthus retroflexus*), common purslane (*Portulaca oleracea*), smart weed sp. (*Poligonum sp.*), common lambsquarter (*Chenopodium album*), and weeds in paddy fields such as false pimpernel (*Lindernia pyxidaria*), monochloria (*Monochoria vaginalis Presl.*) and toothcup (*Rotala indica Koehue*); sedge weeds such as nutsedge sp. (*Cuperus difformis*) and slender spikerush (*Eleocharis acicularis*).

One of the most important properties of herbicides is that they be able to display a herbicidal activity on various kinds of weeds, because, if they can control most kinds of weed but not a few other kinds of weed, the remaining weeds will often grow and do harm to crops.

Therefore, the compounds of the present invention, which can display a strong herbicidal activity on more kinds of weed, can be said most suitable for a herbicide.

As for the insecticidal effect of the present compounds, they have a strong controlling effect on insects injurious to agriculture such as aphids, stem-borers and armyworms and cutworms; insects injurious to sanitation such as cockroaches, and houseflies; insects injurious to stored cereals; mites; and nematodes. Consequently they can be effectively used as a herbicide, insecticide, acaricide and nematocide.

The present invention rlates to a herbicide, insecticide, acaricide and nematocide based on the above-mentioned information which contain the compounds represented by the formula (I) as an active ingredient.

Belgian Patent No. 767,132 indicates that phosphorodithiolate compounds having an unsubstituted piperidine moiety have insecticidal, acaricidal and nematocidal activity, but the present inventors have found that azepine compounds and tetrahydro quinoline compounds have unexpected excellent herbicidal activity. This is unobvious from the prior art.

The present invention (1) relates to a compound having herbicidal, insecticidal, acaricidal and nematocidal activity based on the above-mentioned information.

The present invention (3) relates to a herbicidal, insecticidal, acaricidal and nematocidal composition based on the above-mentioned information which contain the compound represented by the formula (I) as an active ingredient.

The present invention (2) relates to a method for producing a compound of the formula (I) with a herbicidal, insecticidal, acaricidal and nematocidal activity characterized in that phosphorodithiolate of the formula;

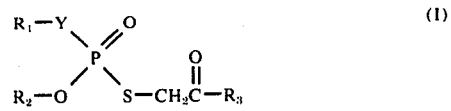

wherein $R_1$, $R_2$, $R_3$ and Y are the same as defined above, is obtained by condensing a salt of thiophosphate of the formula,

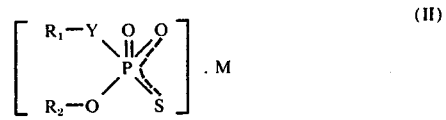

wherein $R_1$, $R_2$, Y and M are the same as defined above, with a halogenated acetoamide compound of the formula,

wherein Hal and $R_3$ are the same as defined above.

The present process can preferably be carried out by condensing a salt of dithiophosphate of the formula (II) with halogenated acetamide compound of the formula (III) in the presence of solvents such as water, alcohols, ketones and if possible solvents which can dissolve both starting materials completely therein. The reaction temperatures and reaction times vary depending upon the kinds of solvent and starting material, and in general the reaction can satisfactorily proceed at 20° to 100 C. for 1 to several hours. On completion of the reaction, the objective products can readily be obtained in a very high purity by conventional treatments, however, if necessary, can further be purified by column-chromatography.

Some examples of the starting materials, i.e., dithiophosphate salts, which are used in the practice of the present invention will be shown as follows.
  potassium O-ethyl-S-n-propylphoshorodithioate
  potassium O-ethyl-S-iso-propylphosphorodithioate
  potassium O-ethyl-S-butylphosphorodithioate
  potassium O-ethyl-S-sec.-butylphosphorodithioate
  potassium O-ethyl-S-iso-butylphosphorodithioate
  potassium O-ethyl-S-ethylphosphorodithioate
  potassium O-ethyl-S-methylphosphorodithioate
  potassium O-ethyl-S-iso-amylphosphorodithioate
  potassium O-ethyl-S-n-octylphosphorodithioate
  potassium O-ethyl-S-allylphosphorodithioate
  potassium O-ethyl-S-propargylphosphorodithioate
  potassium O-ethyl-S-methallylphosphorodithioate
  potassium O-n-propyl-S-n-propylphosphorodithioate
  potassium O-n-propyl-S-n-butylphosphorodithioate
  potassium O-n-propyl-S-allylphosphorodithioate
  potassium O-n-propyl-S-iso-propylphosphorodithioate
  potassium O-n-propyl-S-sec-butylphosphorodithioate
  sodium O-n-butyl-S-ethylphosphorodithioate
  sodium O-n-butyl-S-n-propylphosphorodithioate sodium O-n-butyl-S-iso-propylphosphorodithioate
sodium O-n-amyl-S-n-propylphosphorodithioate
sodium O-methyl-S-n-propylphosphorodithioate
sodium O-methyl-S-n-butylphosphorodithioate
sodium O-methyl-S-iso-propylphosphorodithioate
sodium O-ethyl-S-n-propylphosphorodithioate
sodium O-ethyl-S-n-butylphosphorodithioate
sodium O-ethyl-S-iso-propylphosphorodithioate
sodium O-ethyl-S-sec-butylphosphorodithioate
sodium O-n-propyl-S-n-propylphosphorodithioate
sodium O-n-propyl-S-n-butylphosphorodithioate Next, some representative examples of the organo phosphoric acid ester of the present invention will concretely be shown as follows.

1. 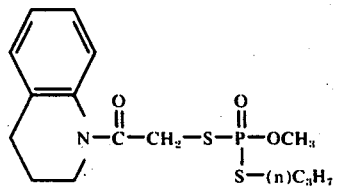

2. 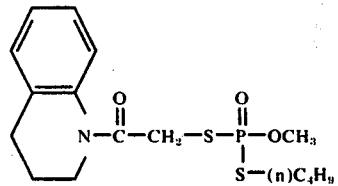

3. 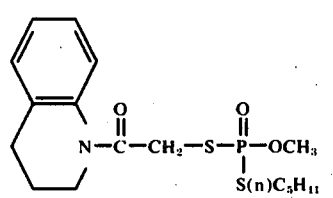

4. 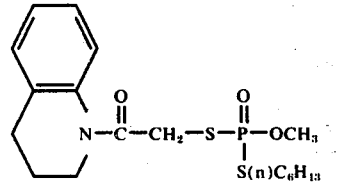

5. 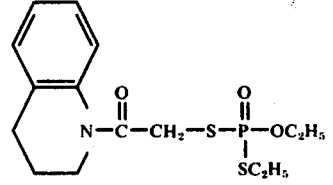

6. 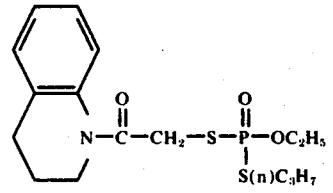

7. 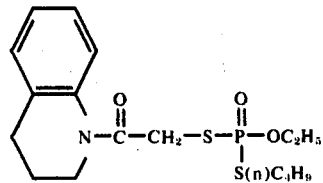

8. 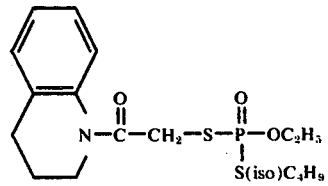

9. 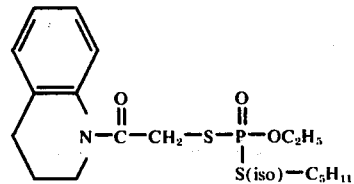

10. 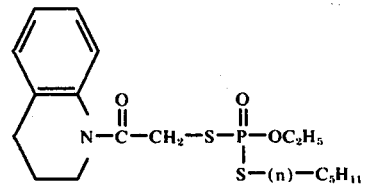

11. 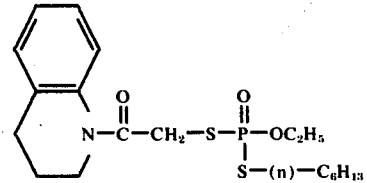

12. 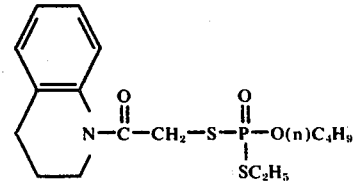

13. 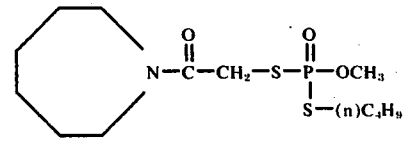

14. 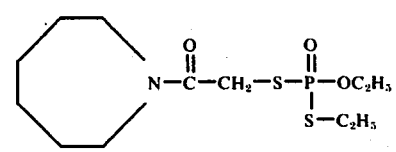

15. 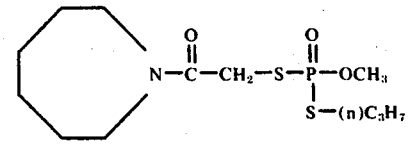

-continued

The compounds of the present invention, as described above, display a strong herbicidal activity on various kinds of weed, however one of the most noticeable features thereof is their herbicidal activity on more kinds of weed. Moreover, the compounds of the present invention have other excellent properties as a herbicide, for example, a long persistency, an activity on both a pre-emergence treatment and a foliage treatment of weeds, and a selectivity to many crops such as rice plant, radish, soy bean, pea, tomato, wheat and corn. The present compounds are also useful as herbicide for use in rice paddy fields, cereal fields, vegetable fields, orchards, turfs, pasture lands, woods and forests and non-crop lands.

The features of the present compounds as an insecticide, acaricide and nematocide are that they have a controlling effect on various kinds of insect, a wide insecticidal spectrum, a particularly strong lethal effect on insects of *Lepidoptera* such as stem-borers and armyworms and cutworms, a strong lethal effect both when applied by spraying or dusting and in soil treatment, and a long persistency.

The present compounds, in actual application thereof, may be used as they are or may be used in any preparation form of dusts, granules, fine granules, wettable powders and emulsifiable concentrates. In formulating those preparations, there are used solid carriers including talc, bentonite, clay, kaolin, diatomaceous earth, vermiculite and calcium hydroxide; and liquid carriers including benzene, alcohols, acetone, xylene, methylnaphthalene, dioxane and cyclohexanone.

In actual application, the present compounds may be enhanced and ensured in effectiveness by using them in combination with surfactants such as spreaders for agriculture. It is also possible to use the present compounds in combination with agricultural chemicals such as fungicides, microbial insecticides, prethroide type insecticides, other insecticides and other herbicides, or with fertilizers.

The compositions of the present invention will be illustrated with reference to the following preparatiobn examples.

PREPARATION 1

25 parts of the compound (1), 5 parts of a surfactant of plyoxyethylene acetylallylester type and 70 parts of talc were thoroughly mixed together by pulverizing to obtain a wettable powder.

PREPARATION 2

30 parts of the compound (3), 20 parts of a surfactant of polyethylene glycolester type and 50 parts of cyclohexanone were thoroughly mixed together to obtain an emulsifiable concentrate.

PREPARATION 3

30 parts of the compound (2), 20 parts of a surfactant of polyethylene glycolester type and 50 parts of cyclohexanone were thoroughly mixed together to obtain an emulsifiable concentrate.

PREPARATION 4

5 parts of the compound (17), 40 parts of bentonite, 50 parts of clay and 5 parts of sodium lignosulfonate were thoroughly mixed together by pulverizing, sufficiently kneaded with water, granulated and dried to obtain granules.

PREPARATION 5

5 parts of the compound (32), 4 parts of sodium lignoslfonate, 86 parts of clay and 5 parts of water were thoroughly kneaded in a ribbon mixer and dried to obtain fine granules.

The present invention will be illustrated in more details with references to the following test examples, in which the names of compound are represented by the numbers of the compounds exemplified above.

TEST EXAMPLE 1

Pre-emergence application

Seeds of barnyard grass (*Echinochloa Crus-galli*) and large crabgrass (*Digitaria sanguinalis*) as representatives of grassy weeds and those of radish, redroot pigweed (*Amaranthus retroflexus*), common purslane (*Portulaca oleracea*) and common lambsquarter (*Chenopodium album*) as representatives of broad-leaved weeds are individually sowed in flower pots of about 10 cm. in diameter. After covering the seeds with soil, test compounds as shown in Table 1 were individually applied to the soil. Thereafter the plants were grown in a green house and 20 days after application the herbicidal effects of the compounds were observed, the results of which are as shown in Table 1.

Herbicidal effects were evaluated by the numerals ranging from 0 (not damaged) to 5 (completely killed). All the test compounds were used in the form of wettable powder and diluted with water before application.

Table 1

| Compound No. | Amount applied (g/a.) | Barnyard grass | Large crabgrass | Radish | Redroot pigweed | Common purslane | Common lambsquarter |
| --- | --- | --- | --- | --- | --- | --- | --- |
|   | 40 | 5 | 5 | 0 | 5 | 5 | 5 |
| 1 | 20 | 5 | 5 | 0 | 4 | 4 | 4 |
|   | 10 | 5 | 5 | 0 | 3 | 3 | 4 |
|   | 40 | 5 | 5 | 0 | 5 | 5 | 5 |
| 2 | 20 | 5 | 5 | 0 | 4 | 4 | 4 |
|   | 10 | 5 | 5 | 0 | 4 | 4 | 4 |
|   | 40 | 5 | 5 | 0 | 5 | 4 | 4 |
| 3 | 20 | 5 | 5 | 0 | 4 | 3 | 4 |
|   | 10 | 4 | 5 | 0 | 3 | 3 | 3 |
|   | 40 | 5 | 5 | 0 | 4 | 4 | 3 |
| 4 | 20 | 4 | 5 | 0 | 4 | 3 | 3 |
|   | 10 | 4 | 4 | 0 | 3 | 3 | 3 |
|   | 40 | 5 | 5 | 1 | 5 | 5 | 5 |
| 5 | 20 | 5 | 5 | 0 | 5 | 5 | 5 |
|   | 10 | 5 | 5 | 0 | 5 | 5 | 5 |
|   | 40 | 5 | 5 | 0 | 5 | 5 | 5 |
| 6 | 20 | 5 | 5 | 0 | 4 | 4 | 4 |
|   | 10 | 5 | 5 | 0 | 4 | 3 | 4 |
|   | 40 | 5 | 5 | 0 | 5 | 5 | 5 |

Table 1-continued

| Compound No. | Amount applied (g/a.) | Barn-yard grass | Large crab-grass | Radish | Redroot pigweed | Common purs-lane | Common lambs-quarter |
|---|---|---|---|---|---|---|---|
| 7 | 20 | 5 | 5 | 0 | 4 | 4 | 4 |
|  | 10 | 5 | 5 | 0 | 4 | 4 | 4 |
|  | 40 | 5 | 5 | 0 | 5 | 5 | 5 |
| 8 | 20 | 5 | 5 | 0 | 4 | 4 | 4 |
|  | 10 | 5 | 5 | 0 | 4 | 3 | 4 |
|  | 40 | 5 | 5 | 0 | 5 | 5 | 5 |
| 9 | 20 | 5 | 5 | 0 | 4 | 4 | 4 |
|  | 10 | 5 | 5 | 0 | 4 | 4 | 3 |
|  | 40 | 5 | 5 | 0 | 5 | 4 | 4 |
| 10 | 20 | 5 | 5 | 0 | 4 | 4 | 4 |
|  | 10 | 4 | 5 | 0 | 3 | 3 | 3 |
|  | 40 | 5 | 5 | 0 | 4 | 4 | 4 |
| 11 | 20 | 4 | 4 | 0 | 4 | 3 | 3 |
|  | 10 | 4 | 4 | 0 | 3 | 3 | 3 |
|  | 40 | 5 | 5 | 0 | 5 | 4 | 4 |
| 12 | 20 | 5 | 5 | 0 | 4 | 4 | 4 |
|  | 10 | 4 | 5 | 0 | 4 | 3 | 3 |
|  | 40 | 5 | 5 | 0 | 5 | 5 | 5 |
| 13 | 20 | 5 | 5 | 0 | 5 | 5 | 5 |
|  | 10 | 5 | 5 | 0 | 5 | 4 | 5 |
|  | 40 | 5 | 5 | 1 | 5 | 5 | 5 |
| 14 | 20 | 5 | 5 | 0 | 5 | 5 | 5 |
|  | 10 | 5 | 5 | 0 | 5 | 5 | 5 |
|  | 40 | 5 | 5 | 1 | 5 | 5 | 5 |
| 15 | 20 | 5 | 5 | 0 | 5 | 5 | 5 |
|  | 10 | 5 | 5 | 0 | 5 | 5 | 5 |
|  | 40 | 5 | 5 | 0 | 5 | 5 | 5 |
| 16 | 20 | 5 | 5 | 0 | 5 | 5 | 5 |
|  | 10 | 5 | 5 | 0 | 5 | 5 | 4 |
|  | 40 | 5 | 5 | 0 | 5 | 5 | 5 |
| 17 | 20 | 5 | 5 | 0 | 5 | 5 | 5 |
|  | 10 | 5 | 5 | 0 | 5 | 4 | 4 |
|  | 40 | 5 | 5 | 0 | 5 | 5 | 5 |
| 18 | 20 | 5 | 5 | 0 | 5 | 5 | 5 |
|  | 10 | 5 | 5 | 0 | 5 | 4 | 5 |
|  | 40 | 5 | 5 | 0 | 5 | 5 | 5 |
| 19 | 20 | 5 | 5 | 0 | 4 | 4 | 5 |
|  | 10 | 4 | 5 | 0 | 4 | 4 | 4 |
|  | 40 | 5 | 5 | 0 | 4 | 4 | 4 |
| 20 | 20 | 4 | 4 | 0 | 4 | 4 | 4 |
|  | 10 | 3 | 4 | 0 | 3 | 4 | 3 |
|  | 40 | 5 | 5 | 0 | 4 | 4 | 4 |
| 21 | 20 | 4 | 5 | 0 | 4 | 4 | 4 |
|  | 10 | 4 | 4 | 0 | 3 | 3 | 3 |
|  | 40 | 5 | 5 | 0 | 4 | 4 | 4 |
| 22 | 20 | 4 | 5 | 0 | 4 | 4 | 4 |
|  | 10 | 4 | 4 | 0 | 3 | 3 | 3 |
|  | 40 | 5 | 5 | 1 | 5 | 5 | 5 |
| 23 | 20 | 5 | 5 | 0 | 5 | 5 | 5 |
|  | 10 | 5 | 5 | 0 | 5 | 5 | 5 |
|  | 40 | 5 | 5 | 0 | 4 | 4 | 4 |
| 24 | 20 | 5 | 5 | 0 | 4 | 4 | 4 |
|  | 10 | 5 | 5 | 0 | 3 | 3 | 3 |
|  | 40 | 5 | 5 | 0 | 5 | 5 | 5 |
| 25 | 20 | 5 | 5 | 0 | 4 | 4 | 4 |
|  | 10 | 5 | 5 | 0 | 4 | 4 | 4 |
|  | 40 | 5 | 5 | 0 | 5 | 5 | 5 |
| 26 | 20 | 5 | 5 | 0 | 5 | 5 | 5 |
|  | 10 | 5 | 5 | 0 | 4 | 4 | 4 |
|  | 40 | 5 | 5 | 0 | 4 | 4 | 3 |
| 27 | 20 | 5 | 5 | 0 | 4 | 3 | 3 |
|  | 10 | 4 | 5 | 0 | 3 | 3 | 3 |
|  | 40 | 5 | 5 | 1 | 4 | 4 | 4 |
| 28 | 20 | 5 | 5 | 0 | 4 | 4 | 3 |
|  | 10 | 4 | 5 | 0 | 3 | 3 | 3 |
|  | 40 | 5 | 5 | 0 | 5 | 5 | 5 |
| 29 | 20 | 5 | 5 | 0 | 4 | 4 | 4 |
|  | 10 | 5 | 5 | 0 | 3 | 3 | 4 |
|  | 40 | 5 | 5 | 0 | 5 | 5 | 5 |
| 30 | 20 | 5 | 5 | 0 | 5 | 4 | 4 |
|  | 10 | 5 | 5 | 0 | 4 | 4 | 4 |
|  | 40 | 5 | 5 | 0 | 4 | 4 | 4 |
| 31 | 20 | 5 | 5 | 0 | 4 | 4 | 4 |
|  | 10 | 5 | 5 | 0 | 4 | 3 | 3 |
|  | 40 | 5 | 5 | 0 | 5 | 5 | 5 |
| 32 | 20 | 5 | 5 | 0 | 4 | 4 | 4 |
|  | 10 | 5 | 5 | 0 | 4 | 4 | 3 |
|  | 40 | 5 | 5 | 0 | 5 | 5 | 5 |
| 33 | 20 | 5 | 5 | 0 | 4 | 4 | 4 |
|  | 10 | 5 | 5 | 0 | 3 | 3 | 3 |
| & PCP[1] | 100 | 3 | 4 | 4 | 4 | 4 | 4 |
| (control) | 50 | 2 | 2 | 1 | 2 | 2 | 2 |
| Zytron[2] | 40 | 4 | 3 | 0 | 1 | 2 | 2 |
| (control) | 20 | 3 | 1 | 0 | 0 | 1 | 0 |

Note:

Table 1-continued

| Compound No. | Amount applied (g/a.) | Barnyard grass | Large crabgrass | Radish | Redroot pigweed | Common purslane | Common lambsquarter |
|---|---|---|---|---|---|---|---|

1) chemical structure: 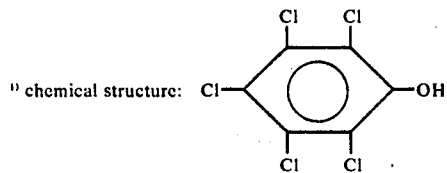

2) chemical structure: 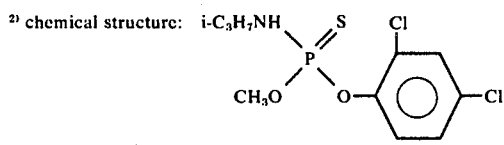

TEST EXAMPLE 2

Water application

Wagner pots of 14 cm. in diameter, which had been packed with 1.5 kg. of paddy field soil, were brought into the state of paddy fields. To the pots were transplanted rice seedlings at the 3-leave stage. Further, seeds of barnyard grass (*Echinochloa Crus-galli*) were sowed in the pots and required amounts of test compounds were applied to the soil under water lodged condition. 25 days after application, the degrees of herbicidal activity and phytotoxicity were investigated on above-mentioned plants which had been transplanted and sowed, and on broad-leaved weeds, e.g., monochoria (*Monochoria Vaginalis Presl.*), false pimpernel (*Lindernia pyxidaria*) and toothcup (*Rotala indica Koehue*), which had been spontaneously germinated. The test compounds were used in the form of wettable powder. The results obtained are as shown in Table 2. The herbcidal effects and the phytotoxity were evaluated as follows by the numerals ranging from 0 to 5.

TABLE 2

| | Effect on plants |
|---|---|
| 0 | No effect. |
| 1 | Very slightly affected. |
| 2 | Slightly affected. |
| 3 | Moderately affected. |
| 4 | Considerably affected. |
| 5 | Completely killed. |

| Compound No. | Amount applied (g/a.) | Herbicidal effects Barnyarn grass | Broad-leaved weeds | Phytotoxicity on rice |
|---|---|---|---|---|
| 1 | 20 | 5 | 5 | 0 |
|   | 10 | 5 | 5 | 0 |
|   | 5 | 5 | 4 | 0 |
| 2 | 20 | 5 | 5 | 0 |
|   | 10 | 5 | 4 | 0 |
|   | 5 | 5 | 4 | 0 |
| 3 | 20 | 5 | 5 | 0 |
|   | 10 | 5 | 4 | 0 |
|   | 5 | 4 | 4 | 0 |
| 4 | 20 | 5 | 5 | 0 |
|   | 10 | 4 | 4 | 0 |
|   | 5 | 4 | 3 | 0 |
| 5 | 20 | 5 | 5 | 1 |
|   | 10 | 5 | 5 | 0 |
|   | 5 | 5 | 5 | 0 |
| 6 | 20 | 5 | 5 | 0 |
|   | 10 | 5 | 5 | 0 |
|   | 5 | 5 | 4 | 0 |
| 7 | 20 | 5 | 5 | 0 |
|   | 10 | 5 | 5 | 0 |
|   | 5 | 5 | 4 | 0 |
| 8 | 20 | 5 | 5 | 0 |
|   | 10 | 5 | 5 | 0 |
|   | 5 | 5 | 4 | 0 |

TABLE 2-continued

| Compound No. | Amount applied (g/a.) | Barnyarn grass | Broad-leaved weeds | Phytotoxicity on rice |
|---|---|---|---|---|
| 9 | 20 | 5 | 5 | 0 |
|   | 10 | 5 | 5 | 0 |
|   | 5 | 5 | 4 | 0 |
| 10 | 20 | 5 | 5 | 0 |
|    | 10 | 5 | 4 | 0 |
|    | 5 | 4 | 4 | 0 |
| 11 | 20 | 4 | 4 | 0 |
|    | 10 | 4 | 4 | 0 |
|    | 5 | 4 | 3 | 0 |
| 12 | 20 | 5 | 5 | 0 |
|    | 10 | 4 | 4 | 0 |
|    | 5 | 4 | 4 | 0 |
| 13 | 20 | 5 | 5 | 0 |
|    | 10 | 5 | 5 | 0 |
|    | 5 | 5 | 5 | 0 |
| 14 | 20 | 5 | 5 | 1 |
|    | 10 | 5 | 5 | 0 |
|    | 5 | 5 | 5 | 0 |
| 15 | 20 | 5 | 5 | 1 |
|    | 10 | 5 | 5 | 0 |
|    | 5 | 5 | 5 | 0 |
| 16 | 20 | 5 | 5 | 0 |
|    | 10 | 5 | 5 | 0 |
|    | 5 | 5 | 5 | 0 |
| 17 | 20 | 5 | 5 | 0 |
|    | 10 | 5 | 5 | 0 |
|    | 5 | 5 | 5 | 0 |
| 18 | 20 | 5 | 5 | 0 |
|    | 10 | 5 | 5 | 0 |
|    | 5 | 5 | 5 | 0 |
| 19 | 20 | 5 | 4 | 0 |
|    | 10 | 5 | 4 | 0 |
|    | 5 | 4 | 4 | 0 |
| 20 | 20 | 5 | 4 | 0 |
|    | 10 | 4 | 4 | 0 |
|    | 5 | 4 | 3 | 0 |
| 21 | 20 | 5 | 5 | 0 |
|    | 10 | 4 | 4 | 0 |
|    | 5 | 4 | 3 | 0 |
| 22 | 20 | 5 | 5 | 0 |
|    | 10 | 4 | 4 | 0 |
|    | 5 | 4 | 3 | 0 |
| 23 | 20 | 5 | 5 | 0 |
|    | 10 | 5 | 5 | 0 |
|    | 5 | 5 | 5 | 0 |
| 24 | 20 | 5 | 5 | 0 |
|    | 10 | 5 | 5 | 0 |
|    | 5 | 5 | 5 | 0 |
| 25 | 20 | 5 | 5 | 0 |
|    | 10 | 5 | 5 | 0 |
|    | 5 | 5 | 5 | 0 |
| 26 | 20 | 5 | 5 | 0 |
|    | 10 | 5 | 5 | 0 |
|    | 5 | 5 | 5 | 0 |
| 27 | 20 | 5 | 5 | 0 |
|    | 10 | 5 | 5 | 0 |
|    | 5 | 5 | 4 | 0 |
| 28 | 20 | 5 | 5 | 0 |
|    | 10 | 5 | 5 | 0 |
|    | 5 | 5 | 4 | 0 |
| 29 | 20 | 5 | 5 | 0 |
|    | 10 | 5 | 5 | 0 |
|    | 5 | 5 | 4 | 0 |
| 30 | 20 | 5 | 5 | 0 |
|    | 10 | 5 | 5 | 0 |
|    | 5 | 5 | 5 | 0 |
| 31 | 20 | 5 | 5 | 0 |
|    | 10 | 5 | 5 | 0 |

TABLE 2-continued

| | | | | |
|---|---|---|---|---|
| | 5 | 5 | 5 | 0 |
| | 20 | 5 | 5 | 0 |
| 32 | 10 | 5 | 5 | 0 |
| | 5 | 5 | 5 | 0 |
| | 20 | 5 | 5 | 0 |
| 33 | 10 | 5 | 5 | 0 |
| | 5 | 5 | 5 | 0 |
| PCP | 100 | 5 | 5 | 3 |
| (control) | 50 | 4 | 5 | 2 |
| Zytron | 40 | 3 | 3 | 0 |
| (control) | 20 | 1 | 2 | 0 |
| NIP[1] | 40 | 5 | 5 | 4 |
| (control) | 20 | 5 | 5 | 2 |

Note:
[1]Chemical structure:

Cl-[benzene ring with Cl]-O-[benzene ring]-NO$_2$

TEST EXAMPLE 3

Lethal effect on carmine mite (*Tetranychus telarius*)

A large number of carmine mite adults were made parasitic on leaves of potted kidney beans at a 2-leave stage which had elapsed 10 days after sowing. The leaves of kidney bean on which carmine mites had been made parasitic were dipped for 1 minute in each aqueous solution of the present compounds of wettable powder type. Water was given to the leaves so as not to kill them, and after 48 hours the number of dead and live mites were observed microscopically to calculate the mortality. Values of LC$_{50}$ were obtained from the mortality. The results are as shown in Table 3.

Table 3

| Compound No. | LC$_{50}$ (ppm) |
|---|---|
| 2 | 9.1 |
| 8 | 13.5 |
| 9 | 52.6 |
| 15 | 16.1 |
| 17 | 50.8 |
| 18 | 36.7 |
| & Smite[1] (control) | 102.0 |

Note:
[1]Chemical structure:

t-C$_4$H$_9$-[benzene ring]-OCH$_2$CH(CH$_3$)OCH$_2$CH(CH$_3$)OS(=O)OC$_2$H$_4$Cl

TEST EXAMPLE 4

Lethal effect on tobacco cut worm (*Spodoptera litura*)

The present compounds of an emulsifiable concentrate type were applied to leaves of chinese cabbage in the form of a 1,000 fold dilute solution. After air-drying, third to fourth instar larvae of tobacco cut worm were released and after 48 hours the number of dead and live were observed. The results are as shown in Table 4.

Table 4

| Compound No. | Mortality (%) |
|---|---|
| 1 | 83.5 |
| 2 | 70 |
| 7 | 85.0 |
| 8 | 100 |
| 15 | 84.2 |
| 17 | 70.0 |

Table 4-continued

| Compound No. | Mortality (%) |
|---|---|
| 18 | 93.1 |
| EPN[1] (control) | 70.0 |

Note:
[1]Chemical structure: C$_2$H$_5$O-P(=S)(-[benzene ring])-O-[benzene ring]-NO$_2$

TEST EXAMPLE 5

Lethal effect on rice stem borer (*Chilo suppressalis*)

Eggs, just before hatching, of the rice stem borer were applied in a ratio of 100/pot near the root of rice plants grown up into the tillering stage in an 1/50000 a Wagner's pot. After eggs were hatched and the larvae entered into stems of rice plants, a 1,000 fold dilute solution of each 50 % emulsifiable concentrate of the present compounds was applied by means of a turn table. The number of dead and alive were observed to calculate the mortality 4 days after application. The results are as shown in Table 5.

Table 5

| Compound No. | Mortality (%) |
|---|---|
| 15 | 85.6 |
| 17 | 98.7 |
| Malathion[1] (control) | 41.3 |

Note:
[1]Chemical structure:

(CH$_3$O)$_2$P(=S)-S-CH(CO$_2$C$_2$H$_5$)-CH$_2$-CO$_2$C$_2$H$_5$

TEST EXAMPLE 6

Effect on nematode 0.5 ml. of a nematode-containing aqueous solution separated from food according to Baermann's method was placed in a test tube with ground stopper containing 0.5 ml. of an aqueous dilute solution of each emulsifiable concentrate of the present compounds. The concentration of the active ingredient in the mixture was adjusted to 500 p.p.m. After 24 hours, the number of dead and alive were observed microscopically to calculate the mortality. The results are as shown in Table 6.

Table 6

| Compound No. | Mortality (%) |
|---|---|
| 1 | 100 |
| 2 | 100 |
| 6 | 100 |
| 7 | 100 |
| 8 | 100 |
| 9 | 100 |
| 13 | 100 |
| 14 | 85.7 |
| 15 | 100 |
| 16 | 100 |
| 17 | 100 |
| 18 | 100 |
| Dichloropropane[1] | 79.3 |

| | -continued | |
|---|---|---|
| Calculated (%) (as $C_{15}H_{22}NO_3PS_2$) | | Found % |
| P | 8.64 | 8.66 |

EXAMPLE 2

(Compound No. 8)

To a solution of 6.60 g. of potassium O-ethyl-S-i-butylphosphorodithioate in 50 ml. of ethanol, were added 5.40 g. of N-chloroacetyltetrahydroquinoline. The mixture was heated under reflux at 80° C. for 2 hours, and cooled to room temperature to separate potassium chloride which was then filtered off. Ethanol was distilled off from the filtrate and then the residual oily matter was dissolved in 50 ml. of benzene, washed with a 5 % sodium bicarbonate solution and then water, and dried over anhydrous calcium chloride. Thereafter benzene was distilled off under reduced pressure to obtain 9.6 g. of N-(O-ethyl-S-i-butyldithiolphosphorylacetyl)-tetrahydroquinoline ($n_D^{28}$ 1.5700).

Elemental analysis:

| | Calculated (%) (as $C_{17}H_{26}NO_3PS_2$) | Found (%) |
|---|---|---|
| C | 52.71 | 52.82 |
| H | 6.72 | 6.74 |
| N | 3.62 | 3.57 |
| P | 8.01 | 8.13 |

EXAMPLE 3

(Compound No. 14)

To a solution of 7.84 g. of potassium O,S-diethyl-phosphorodithioate in 50 ml. of acetone, were added 5.44 g. of N-chloroacetylhexamethylene imine. The mixture was heated under reflux at 60° C. for 3 hours, and cooled to room temperature to separate potassium chloride which was then filtered off. Acetone was distilled off from the filtrate and then the residual oily matter was distilled in 50 ml. of benzene, washed with a 5 % sodium bicarbonate solution and then water, and dried over anhydrous calcium chloride. Thereafter benzene was distilled off under reduced pressure to obtain 9.50 g. of oily N-(O,S-diethyldithiolphosphorylacetyl)-hexamethylene imine ($n_D^{29}$ 1.5349). The yield was 94 % based on N-chloroacetylhexamethylene imine.

Elemental analysis:

| | Calculated (%) (as $C_{12}H_{24}NO_3PS_2$) | Found (%) |
|---|---|---|
| C | 44.31 | 44.10 |
| H | 7.38 | 7.31 |
| N | 4.31 | 4.39 |
| P | 9.54 | 9.22 |

EXAMPLE 4

(Compound No. 18)

To a solution of 7.08 g. of potassium O-ethyl-S-sec-butylphosphorodithioate in 50 ml. of ethanol, were added 4.91 g. of N-chloroacetylhexamethylene imine. The mixture was heated under reflux at 80° C. for 2

---

Table 6-continued

| Compound No. | Mortality (%) |
|---|---|
| (control) | |

Note:
[1]Chemical structure: $ClCH=CH-CH_2Cl$

TEST EXAMPLE 7

Lethal effect on tobacco cut worm (*Spodoptera litura*) and diamond-back moth (*Plutella maculipennis*)

A 3 % dust of each compound of the present invention was applied, in a proportion of 5 kg./10 a, to the field of cabbage where a large number of tobacco cut worm and diamond-back moth were generated. After 7 days, 20 cabbages were pulled out and the number of insects thereon were checked. The results are as shown in Table 7.

Table 7

| | Number of insects | |
|---|---|---|
| Compound No. | tobacco cut worm | diamond-back moth |
| 15 | 13 | 18 |
| 18 | 9 | 36 |
| No treatment | 47 | 158 |
| Bipterex [1] (control) | 19 | 49 |

[1]Chemical structure:

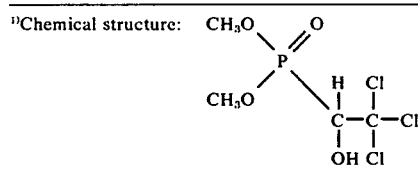

The treated cabbages suffered only the same feeding damage as before dusting, however with the untreated cabbages only leaf veins were left.

The synthetic method according to the present invention will be illustrated with reference to the following examples which are only illustrative but not limitative thereto.

EXAMPLE 1

(Compound No. 5)

To a solution of 7.84 g. of potassium O,S-diethyl-phosphorodithioate in 50 ml. of acetone, were added 6.29 g. of N-chloroacetyltetrahydroquinoline. The mixture was heated under reflux at 60° C. for 3 hours, and cooled to room temperature to separate potassium chloride which was then filtered off. Acetone was distilled off from the filtrate and then the residual oily matter was dissolved in 50 ml. of benzene, washed with a 5 % sodium bicarbonate solution and then water, and dried over anhydrous calcium chloride. Thereafter benzene was distilled off under reduced pressure to obtain 10.1 g. of N-(O,S-diethyldithiolphosphorylacetyl)tetrahydroquinoline ($n_D^{28}$ 1.5796). The yield was 94.5 % based on N-chloroacetyltetrahydroquinoline.

Elemental analysis:

| | Calculated (%) (as $C_{15}H_{22}NO_3PS_2$) | Found % |
|---|---|---|
| C | 50.14 | 50.19 |
| H | 6.13 | 6.23 |
| N | 3.90 | 3.84 | hours, and cooled to room temperature to separate potassium chloride which was then filtered off. Ethanol was distilled off from the filtrate and then the residual oily matter was dissolved in 50 ml. of benzene, washed with a 5 % sodium bicarbonate solution and then water, and dried over anhydrous calcium chloride. Thereafter benzene was distilled off under reduced pressure to obtain 8.90 g. of N-(O-ethyl-S-sec-butylidithiolphosphorylacetyl)-hexamethylene imine ($n_D^{23}$ 1.5299). The yield was 90 % based on N-chloroacetylhexamethylene imine.

Elemental analysis:

| | Calculated (%) (as $C_{14}H_{28}NO_3PS_2$) | Found (%) |
|---|---|---|
| C | 47.59 | 47.32 |
| H | 7.93 | 8.08 |
| N | 3.97 | 4.01 |
| P | 8.78 | 8.47 |

EXAMPLE 5

(Compound No. 25)

In 50 ml. of acetone were dissolved 5.24 g. (0.025 mol) of N-chloroacetyl-1,2,3,4-tetrahydroquinoline and 7.0 g. (0.026 mol) of potassium O-ethyl-O-metatolyl-phosphorothioate. The mixture was heated under reflux for 2 hours, cooled to room temperature, and then the resulting solid matter was removed by filtration. After removal of the solvent under reduced pressure, the residual oily matter was dissolved in 100 ml. of benzene, washed twice with water, dried over anhydrous calcium chloride and distilled to remove benzene. The residual oily matter was allowed to stand at 90° C. for 1 hour under reduced pressure (0.1 mmHg) to obtain 6.0 g. of an analytically pure objective product ($n_D^{21}$ 1.5804).

Elemental analysis:

| | Calculated (%) (as $C_{20}H_{24}O_4NPS$) | Found (%) |
|---|---|---|
| C | 59.24 | 59.07 |
| H | 5.97 | 6.09 |
| N | 3.46 | 3.56 |
| P | 7.64 | 7.64 |
| S | 7.91 | 8.01 |

EXAMPLE 6

(Compound No. 24)

In 50 ml. of acetone were dissolved 5.45 g. (0.026 mol) of N-chloroacetyl-1,2,3,4-tetrahydroquinoline and 7.2 g. (0.03 mol) of sodium O-ethyl-O-phenylphosphorothioate. The solution was treated in the same manner as described in Example 5 to obtain 5.7 g. of objective product ($n_D^{28}$ 1.5819).

Elemental analysis:

| | Calculated (%) (as $C_{19}H_{22}NO_4PS$) | Found (%) |
|---|---|---|
| C | 58.21 | 58.37 |
| H | 5.63 | 5.56 |
| N | 3.58 | 3.55 |
| P | 7.93 | 7.81 |
| S | 8.18 | 8.23 |

According to the process of the present invention, there are produced such phosphorothiolates as shown in the following table.

| Example No. | Compound No. | Yield (%) | Refractive index | | Elemental analysis Calculated (%) | Found (%) |
|---|---|---|---|---|---|---|
| 7 | 1 | 78.1 | $n_D^{24}$ 1.5832 | C | 50.14 | 49.91 |
| | | | | H | 6.13 | 6.14 |
| | | | | N | 3.90 | 3.98 |
| | | | | P | 8.64 | 8.35 |
| 8 | 2 | 79.2 | $n_D^{28}$ 1.5775 | C | 51.41 | 51.39 |
| | | | | H | 6.43 | 6.39 |
| | | | | N | 3.75 | 3.87 |
| | | | | P | 8.31 | 8.06 |
| 9 | 3 | 80.5 | $n_D^{24}$ 1.5751 | C | 52.71 | 52.48 |
| | | | | H | 6.72 | 6.74 |
| | | | | N | 3.62 | 3.65 |
| | | | | P | 8.01 | 7.98 |
| 10 | 4 | 82.1 | $n_D^{24}$ 1.5656 | C | 53.87 | 53.74 |
| | | | | H | 6.98 | 6.91 |
| | | | | N | 3.49 | 3.39 |
| | | | | P | 7.73 | 7.99 |
| 11 | 6 | 82.2 | $n_D^{24}$ 1.5771 | C | 51.47 | 51.65 |
| | | | | H | 6.43 | 6.49 |
| | | | | N | 3.75 | 3.70 |
| | | | | P | 8.31 | 8.55 |
| 12 | 7 | 83.5 | $n_D^{24}$ 1.5745 | C | 52.71 | 52.47 |
| | | | | H | 6.72 | 6.68 |
| | | | | N | 3.62 | 3.67 |
| | | | | P | 8.01 | 7.91 |
| 13 | 9 | 84.3 | $n_D^{24}$ 1.5669 | C | 53.87 | 53.86 |
| | | | | H | 6.98 | 6.93 |
| | | | | N | 3.49 | 3.47 |
| | | | | P | 7.73 | 7.54 |
| 14 | 10 | 85.2 | $n_D^{25}$ 1.5708 | C | 53.87 | 54.00 |
| | | | | H | 6.98 | 7.10 |
| | | | | N | 3.49 | 3.73 |
| | | | | P | 7.73 | 7.61 |
| 15 | 11 | 80.4 | $n_D^{25}$ 1.5680 | C | 54.94 | 55.13 |
| | | | | H | 7.23 | 7.04 |
| | | | | N | 3.37 | 3.57 |
| | | | | P | 7.47 | 7.59 |

-continued

| Example No. | Compound No. | Yield (%) | Refractive index | | Elemental analysis | | |
|---|---|---|---|---|---|---|---|
| | | | | | | Calculated (%) | Found (%) |
| 16 | 12 | 81.3 | $n_D^{28}$ | 1.5733 | C | 52.71 | 57.55 |
| | | | | | H | 6.72 | 6.68 |
| | | | | | N | 3.62 | 3.68 |
| | | | | | P | 8.01 | 8.13 |
| 17 | 13 | 77.9 | $n_D^{24}$ | 1.5285 | C | 46.02 | 45.62 |
| | | | | | H | 7.67 | 7.57 |
| | | | | | N | 4.13 | 4.17 |
| | | | | | P | 9.14 | 8.73 |
| 18 | 15 | 85.7 | $n_D^{30}$ | 1.5469 | C | 46.02 | 46.06 |
| | | | | | H | 7.67 | 7.93 |
| | | | | | N | 4.13 | 4.10 |
| | | | | | P | 9.14 | 9.30 |
| 19 | 16 | 82.3 | $n_D^{24}$ | 1.5291 | C | 47.59 | 47.67 |
| | | | | | H | 7.93 | 7.98 |
| | | | | | N | 3.97 | 3.89 |
| | | | | | P | 8.78 | 8.40 |
| 20 | 17 | 80.1 | $n_D^{30}$ | 1.5302 | C | 47.59 | 47.48 |
| | | | | | H | 7.93 | 7.69 |
| | | | | | N | 3.97 | 3.90 |
| | | | | | P | 8.78 | 8.72 |
| 21 | 19 | 81.5 | $n_D^{25}$ | 1.5290 | C | 49.05 | 49.20 |
| | | | | | H | 8.17 | 8.20 |
| | | | | | N | 3.81 | 3.87 |
| | | | | | P | 8.45 | 8.50 |
| 22 | 20 | 81.6 | $n_D^{24}$ | 1.5260 | C | 50.39 | 50.20 |
| | | | | | H | 8.40 | 8.49 |
| | | | | | N | 3.67 | 3.73 |
| | | | | | P | 8.14 | 7.84 |
| 23 | 21 | 82.1 | $n_D^{25}$ | 1.5284 | C | 47.59 | 47.60 |
| | | | | | H | 7.93 | 7.97 |
| | | | | | N | 3.97 | 4.07 |
| | | | | | P | 8.78 | 8.51 |
| 24 | 22 | 79.5 | $n_D^{23}$ | 1.5439 | C | 46.27 | 46.55 |
| | | | | | H | 7.17 | 7.38 |
| | | | | | N | 4.15 | 4.23 |
| | | | | | P | 9.18 | 9.31 |
| 25 | 23 | 83.1 | $n_D^{25}$ | 1.5422 | C | 42.44 | 42.62 |
| | | | | | H | 7.07 | 7.01 |
| | | | | | N | 4.50 | 4.59 |
| | | | | | P | 9.97 | 9.85 |
| 26 | 20 | 82.7 | $n_D^{23}$ | 1.5816 | C | 59.24 | 59.20 |
| | | | | | H | 5.97 | 6.05 |
| | | | | | N | 3.46 | 3.45 |
| | | | | | P | | |
| 27 | 27 | 83.5 | $n_D^{22}$ | 1.5803 | C | 60.13 | 60.28 |
| | | | | | H | 6.25 | 6.19 |
| | | | | | N | 3.34 | 3.34 |
| | | | | | P | | |
| 28 | 28 | 81.4 | $n_D^{21}$ | 1.5898 | C | 53.58 | 53.54 |
| | | | | | H | 4.94 | 4.97 |
| | | | | | N | 3.29 | 3.31 |
| | | | | | P | | |

What we claim is:
1. A compound selected from the group consisting of
1. N-(O-methyl-S-n-propyldithiolphosphorylacetyl)-tetrahydroquinoline,
2. N-(O-methyl-S-n-butyldithiolphosphorylacetyl)-tetrahydroquinoline,
3. N-(O-methyl-S-n-pentyldithiolphosphorylacetyl)-tetrahydroquinoline,
4. N-(O-methyl-S-n-hexyldithiolphosphorylacetyl)-tetrahydroquinoline,
5. N-(O-diethyldithiolphosphorylacetyl)-tetrahydroquinoline,
6. N-(O-ethyl-S-n-propyldithiolphosphorylacetyl)-tetrahydroquinoline,
7. N-(O-ethyl-S-n-butyldithiolphosphorylacetyl)-tetrahydroquinoline,
8. N-(O-ethyl-S-iso-butyldithiolphosphorylacetyl)-tetrahydroquinoline,
9. N-(O-ethyl-S-iso-pentyldithiolphosphorylacetyl)-tetrahydroquinoline,
10. N-(O-ethyl-S-n-pentyldithiolphosphorylacetyl)-tetrahydroquinoline,
11. N-(O-ethyl-S-n-hexyldithiolphosphorylacetyl)-tetrahydroquinoline,
12. N-(O-butyl-S-ethyldithiolphosphorylacetyl)-tetrahydroquinoline,
13. N-(O-methyl-S-n-butyldithiolphosphorylacetyl)-hexamethylene imine,
14. N-(O,S-diethyldithiolphosphorylacetyl)-hexamethylene imine,
15. N-(O-ethyl-S-n-propyldithiolphosphorylacetyl)-hexamethylene imine,
16. N-(O-ethyl-S-n-butyldithiolphosphorylacetyl)-hexamethylene imine,
17. N-(O-ethyl-S-iso-butyldithiolphosphorylacetyl)-hexamethylene imine,
18. N-(O-ethyl-S-sec-butyldithiolphosphorylacetyl)-hexamethylene imine,
19. N-(O-ethyl-S-n-pentyldithiolphosphorylacetyl)-hexamethylene imine,
20. N-(O-ethyl-S-n-hexyldithiolphosphorylacetyl)-hexamethylene imine,
21. N-(O-n-butyl-S-ethyldithiolphosphorylacetyl)-hexamethylene imine,

22. N-(O-ethyl-S-allyldithiolphosphorylacetyl)-hexamethylene imine,
23. N-(O-ethyl-S-methyldithiolphosphorylacetyl)-hexamethylene imine,
24. N-(O-ethyl-O-phenylthiolphosphorylacetyl)-tetrahydroquinoline,
25. N-(O-ethyl-O-metatolylthiolphosphorylacetyl)-tetrahydroquinoline,
26. N-(O-ethyl-O-orthotolylthiolphosphorylacetyl)-tetrahydroquinoline,
27. N-(O-ethyl-O-3,5-xylenylthiolphosphorylacetyl)-tetrahydroquinoline,
28. N-(O-ethyl-O-parachlorophenylthiolphosphorylacetyl)-tetrahydroquinoline,
29. N-(O-n-propyl-O-phenylthiolphosphorylacetyl)-tetrahydroquinoline,
30. N-(O-n-propyl-O-orthotolylthiolphosphorylacetyl)-tetrahydroquinoline,
31. N-(O-n-butyl-O-phenylthiolphosphorylacetyl)-tetrahydroquinoline,
32. N-(O-n-butyl-O-metatolylthiolphosphorylacetyl)-tetrahydroquinoline, and
33. N-(O-butyl-O-paraethylphenylthiolphosphorylacetyl)-tetrahydroquinoline.

2. A compound of the formula,

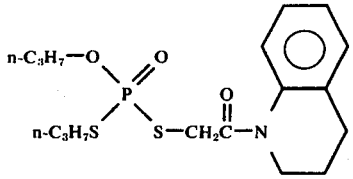

3. A compound of the formula,

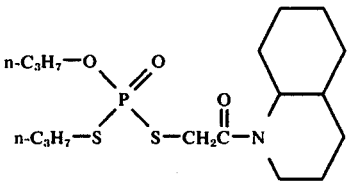

* * * * *

UNITED STATES PATENT OFFICE
CERTIFICATE OF CORRECTION

Patent No. 3,997,526                    Dated December 14, 1976

Inventor(s) TAKEO SATOMI et al.

It is certified that error appears in the above-identified patent and that said Letters Patent are hereby corrected as shown below:

Column 1, lines 55-60, change formula (II) to read as

-- 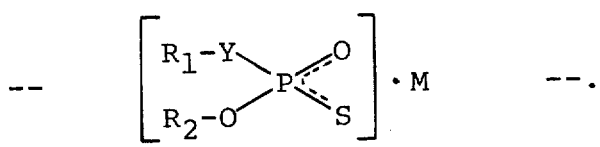 --.

Column 2, lines 10-15, change formula (I-a) to read as

-- 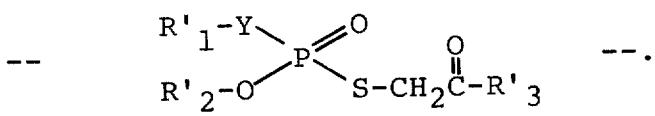 --.

Column 2, lines 24-30, change the second formula to read as

-- 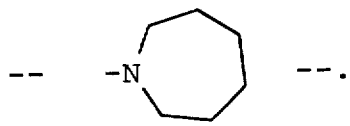 --.

Column 4, lines 17-21, change formula (II) to read as

-- 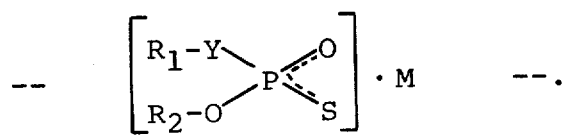 --.

UNITED STATES PATENT OFFICE
CERTIFICATE OF CORRECTION

Patent No. 3,997,526　　　　　　Dated December 14, 1976

Inventor(s) TAKEO SATOMI et al.

It is certified that error appears in the above-identified patent and that said Letters Patent are hereby corrected as shown below:

CONTINUATION

Claim 3, change the formula to read as

-- 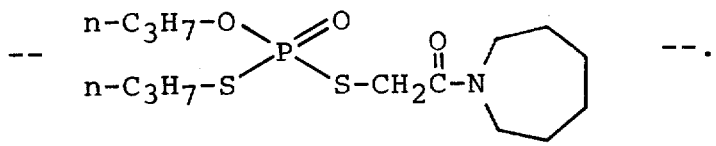 --.

Signed and Sealed this

*ninth* Day of *August 1977*

[SEAL]

*Attest:*

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,997,526
DATED : December 14, 1976
INVENTOR(S) : TAKEO SATOMI et al.

It is certified that error appears in the above-identified patent and that said Letters Patent are hereby corrected as shown below:

Claim 1, compound 5, line 1, change "N-(O-" to -- N-(O,S- --;

compound 12, line 1, change "N-(O-" to -- N-(O-n- --.

*Signed and Sealed this*

*Twenty-second* Day of *January 1980*

[SEAL]

Attest:

SIDNEY A. DIAMOND

*Attesting Officer*

*Commissioner of Patents and Trademarks*